US012721627B2

(12) United States Patent
Lebner

(10) Patent No.: US 12,721,627 B2
(45) Date of Patent: Sep. 1, 2026

(54) INCISION CLOSURE DEVICE

(71) Applicant: CLOZEX MEDICAL, INC., West Bridgewater, MA (US)

(72) Inventor: Michael Lebner, Wellesley Hills, MA (US)

(73) Assignee: CLOZEX MEDICAL, INC., West Bridewater, MA (US)

( * ) Notice: Subject to any disclaimer, the term of this patent is extended or adjusted under 35 U.S.C. 154(b) by 678 days.

(21) Appl. No.: 18/001,993

(22) PCT Filed: Jun. 19, 2020

(86) PCT No.: PCT/US2020/038596

§ 371 (c)(1),
(2) Date: Dec. 15, 2022

(87) PCT Pub. No.: WO2021/257082

PCT Pub. Date: Dec. 23, 2021

(65) Prior Publication Data

US 2023/0363760 A1 Nov. 16, 2023

(51) Int. Cl.
*A61B 17/08* (2006.01)
*A61B 17/00* (2006.01)

(52) U.S. Cl.
CPC .. *A61B 17/085* (2013.01); *A61B 2017/00862* (2013.01); *A61B 2017/00884* (2013.01); *A61B 2017/00951* (2013.01); *A61B 2017/086* (2013.01)

(58) Field of Classification Search
CPC .............. A61B 17/085; A61B 17/0466; A61B 2017/00862; A61B 2017/00884; A61B 2017/00951; A61B 2017/086; A61F 13/0259; A61F 13/02; A61F 13/0246; A61F 13/0236; A61F 2013/00089; A61F 2013/00289
See application file for complete search history.

(56) References Cited

U.S. PATENT DOCUMENTS

| | | | |
|---|---|---|---|
| 6,329,564 | B1 | 12/2001 | Lebner |
| 6,822,133 | B2 | 11/2004 | Lebner |
| 6,831,205 | B2 | 12/2004 | Lebner |

(Continued)

FOREIGN PATENT DOCUMENTS

| | | | |
|---|---|---|---|
| DE | 551713 | C | 6/1932 |
| JP | 2005512678 | A | 5/2005 |

(Continued)

OTHER PUBLICATIONS

Office Action from the Japanese Patent Office dated Mar. 5, 2024 from related Patent Application No. JP 2022-578684.

(Continued)

*Primary Examiner* — Elizabeth Houston
*Assistant Examiner* — Lauren Dubose
(74) *Attorney, Agent, or Firm* — Pierce Atwood LLP; Christopher A. Baxter

(57) ABSTRACT

Disclosed is a two-component device for closing a wound or incision. The two-component device includes a first elongated component and a second elongated component, wherein at least one of the first elongated component or the second elongated component comprises a plurality of lateral translation elements.

12 Claims, 5 Drawing Sheets

(56) References Cited

U.S. PATENT DOCUMENTS

| | | | | |
|---|---|---|---|---|
| 7,332,641 | B2 | 2/2008 | Lebner et al. | |
| 7,354,446 | B2 | 4/2008 | Lebner | |
| 7,414,168 | B2 | 8/2008 | Lebner | |
| 7,511,185 | B2 | 3/2009 | Lebner | |
| 7,563,941 | B2 | 7/2009 | Lebner et al. | |
| 7,838,718 | B2 | 11/2010 | Lebner | |
| 7,981,136 | B2 | 7/2011 | Weiser | |
| 8,636,763 | B2 | 1/2014 | Lebner | |
| 2002/0099315 | A1* | 7/2002 | Lebner | A61B 17/085 602/54 |
| 2005/0021083 | A1* | 1/2005 | Lebner | A61B 17/085 606/216 |
| 2007/0038246 | A1* | 2/2007 | Lebner | A61B 17/085 606/215 |
| 2007/0038247 | A1 | 2/2007 | Lebner et al. | |
| 2010/0228287 | A1 | 9/2010 | Jeekel et al. | |
| 2013/0345744 | A1 | 12/2013 | Weiser | |
| 2019/0343524 | A1 | 11/2019 | Weiser | |
| 2021/0113208 | A1* | 4/2021 | Varadarajan | A61F 13/0236 |

FOREIGN PATENT DOCUMENTS

| | | | |
|---|---|---|---|
| WO | 2003053296 | A1 | 7/2003 |
| WO | 2017052549 | A1 | 3/2017 |
| WO | 2019099801 | A1 | 5/2019 |
| WO | 2019183419 | A1 | 9/2019 |

OTHER PUBLICATIONS

Extended European Search Report dated Feb. 1, 2024, issued in European Patent Application No. 20940506.7.

Communication pursuant to Article 94(3) EPC from the European Patent Office mailed Jan. 16, 2026 for European Patent Application No. 20 940 506.7, 8 pages.

* cited by examiner

INCISION CLOSURE DEVICE

RELATED APPLICATION

This application is a 371 of International Application Number PCT/US20/38596, filed on Jun. 19, 2020. The entire contents of the above application are incorporated herein by reference.

BACKGROUND

ClozeX Medical, LLC is the record owner of numerous issued US and foreign patents relating to two-component wound/incision closure devices including, for example, the following U.S. Pat. Nos. 6,329,564; 6,831,205; 6,822,133; 7,511,185; 8,636,763; 7,414,168; 7,332,641; 7,354,446; 8,636,763; 7,838,718; 7,414,168 and 7,563,941; all of which are incorporated herein by reference. To the extent that the referenced US patents disclose embodiments wherein at least one component of the two-component wound closure device includes a plurality of elongated connectors associated with a pulling element, each of the plurality of elongated connectors are associated with a single pulling element. In practice, this means that the "pull" through the single pulling element can be represented by a single force vector having a magnitude and a direction. This pulling force, as represented by a single force vector, controls the entire wound edge associated with one component of the two component device. A second pulling force, represented as a single force vector, controls the wound edge associated with a second component of the two component device. While this design works well for the closure of relatively short incisions, the alignment and closure of longer wound/incision edges associated, for example, with total knee arthroplasty or total hip arthroplasty, is challenging when the control of the entire wound edge is under the control of a pulling force represented by a single force vector.

Zipline Medical, Inc. also produces a component device for incision closure. Like the ClozeX Medical, LLC technology referred to in the preceding paragraph, the Zipline Medical Inc. technology offers suture-like outcomes at the speed of staples, with the reduced risk of needle stick injury associated with sutures. The Zipline Medical, Inc. incision closure devices are marketed, in part, for application in longer incision procedures such as total knee and total hip arthroplasty.

Embodiments of the Zipline Medical, Inc. component closure devices include a series of beaded cable ties attached to one component and an opposing series of beaded cable tie receivers attached to a second component on the opposing side of the incision to be closed. Instructions for use indicate that the incision edges are pinched together with the thumb and forefinger proximate a cable tie, and the cable tie is then tightened to maintain the local wound edge relationship established by the pinch. This procedure is repeated along the incision to be closed. Once all beaded cable ties are adjusted, the free end of the beaded cable tie is cut off to reduce the possibility of tampering and to minimize interference with dressings or clothing.

The beaded cable tie system described in the preceding paragraphs is undesirable for a number of reasons. First, the cost of the beaded cable tie device is relatively high as compared with more simple systems utilizing simple polymeric sheet material. Second, while excess beaded cable tie is cut off once the device has been applied and adjusted, these cut ends and beaded cable tie elements, nonetheless, are raised above the skin surface to some degree and are more susceptible to catching on clothing or dressing. It is possible to imagine scenarios wherein the closure device is actually pulled loose shortly after surgery or early in the healing process. Also, the beaded cable device is applied at a fixed gap width and can only be tightened in one dimension, providing less precise grasp, control and alignment of the wound edges as compared with prior art devices.

SUMMARY OF THE DISCLOSURE

The present disclosure relates to a two-component device for closing a wound or incision. The two-component device includes a first elongated component comprising: i) a first flat flexible attaching member comprising a wound edge and a lower surface, the lower surface having an adhesive layer, the adhesive layer being protected by one or more release liners prior to application; and ii) one or more first lateral translation elements, each first lateral translation element comprising one or more first elongated connectors attached to a single first pulling element. The two-component device also includes a second elongated component comprising: i) a second flat flexible attaching member comprising a wound edge and a lower surface, the lower surface having an adhesive layer, the adhesive layer being protected by one or more release liners prior to application; and ii) a plurality of second lateral translation elements, each second lateral translation element comprising one or more second elongated connectors attached to a single second pulling element. The two-component device also includes a means for attaching the one or more first elongated connectors to the second flat flexible attaching member during closure, the attachment of the one or more first elongated connectors to the second flat flexible attaching member forming an attached portion and a bridging portion for each attached first elongated connector. The two-component device also includes a means for attaching the one or more second elongated connectors to the first flat flexible attaching member during closure, the attachment of the one or more second elongated connectors to the first flat flexible attaching member forming an attached portion and a bridging portion for each attached second elongated connector.

In other embodiments, the disclosure relates to a two-component device as described above wherein each first lateral translation element is selected from the group consisting of: i) a single first elongated connector and a single first pulling element; and ii) a plurality of first elongated connectors and a single first pulling element.

In other embodiments, the disclosure relates to a two-component device as described above wherein each second lateral translation element is selected from the group consisting of: i) a single second elongated connector and a single second pulling element; and ii) a plurality of second elongated connectors and a single second pulling element.

In other embodiments, the disclosure relates to a two-component device as described above wherein at least the first and second flat flexible attaching members are produced from transparent stock, or from colored or opaque stock.

In other embodiments, the disclosure relates to a two-component device as described above wherein first and second flat flexible attaching members are produced from inelastic stock, or from elastic stock reinforced with an inelastic structural material.

In other embodiments, the disclosure relates to a two-component device as described above wherein first and second flat flexible attaching members are produced from a vapor-permeable stock.

In other embodiments, the disclosure relates to a two-component device as described above wherein the pulling elements and/or attaching members are coded to enable user distinction.

In other embodiments, the disclosure relates to a two-component device as described above wherein the coding comprises an observable geometric distinction.

In other embodiments, the disclosure relates to a two-component device as described above wherein the coding comprises printed indicia.

In other embodiments, the disclosure relates to a two-component device as described above wherein the coding comprises distinguishing colors.

In other embodiments, the disclosure relates to a two-component device as described above wherein pulling elements are removable following application of the device.

In other embodiments, the disclosure relates to a two-component device as described above wherein pulling elements are reinforced with a pull bar.

In other embodiments, the disclosure relates to a two-component device as described above wherein the means for attaching the one or more first and second elongated connectors to the second and first flat flexible attaching member during closure comprises adhesive.

In other embodiments, the disclosure relates to a two-component device as described above wherein the adhesive is provided on the lower surfaces of the first and second elongated connectors.

In other embodiments, the disclosure relates to a two-component device as described above wherein the adhesive provided on the lower surfaces of the first and second flat flexible attaching members is protected by one or more release liners.

In other embodiments, the disclosure relates to a two-component device as described above wherein the release liners are optionally coded to indicate sequence of removal.

In other embodiments, the disclosure relates to a two-component device as described above wherein the adhesive on the lower surface of the first and second flat flexible attaching members is protected by a first and second release liner, the first release liner protecting adhesive along the lower surface adjacent the wound edge, and the second release liner protecting the adhesive along the remaining parallel section of the lower surface separated from the wound edge, the second release liner being separated from the wound edge by the first release liner.

In other embodiments, the disclosure relates to a two-component device as described above wherein the coding comprises printed indicia enabling user distinction between the first and second release liner.

In other embodiments, the disclosure relates to a two-component device as described above wherein the coding comprises distinguishing colors between the first release liner and the second release liner.

In other embodiments, the disclosure relates to a two-component device as described above wherein the first and second flat flexible attaching members are provided with one or more alignment indicators.

In other embodiments, the disclosure relates to a two-component device as described above wherein the first and second flat flexible attaching members are provided with a wound edge bar.

In other embodiments, the disclosure relates to a two-component device as described above wherein the edges of the first and second flat flexible attaching members adjacent the wound or incision are curved or angled to evert the skin edges.

In other embodiments, the disclosure relates to a two-component device as described above wherein a portion of the first and second elongated connectors is cut away to increase unobstructed surface area above the wound or incision thereby facilitating drainage of exudates and application of medication.

In other embodiments, the disclosure relates to a two-component device as described above wherein the elongated connectors are sufficiently spaced-apart to facilitate lateral adjustment of the first elongated component relative to the second elongated component.

In other embodiments, the disclosure relates to a two-component device as described above wherein the first and second flat flexible attaching members are produced from an elastic polymeric material not reinforced with an inelastic structural material.

In other embodiments, the disclosure relates to a two-component device as described above wherein the first and second flat flexible attaching members are made from inelastic material that is altered by mechanical manipulation.

In other embodiments, the disclosure relates to a two-component device as described above wherein the first and second elongated connectors are strap-like such that the width of each is greater than the thickness of each.

In other embodiments, the disclosure relates to a two-component device as described above wherein the attachment of the first and second elongated connectors to the second and first flat flexible attaching members forms an attached portion and a bridging portion for each individual elongated connector, wherein the average width of the bridging portion of each elongated connector is less than the average width of the attached portion.

In other embodiments, the disclosure relates to a two-component device as described above wherein the bridging portions are substantially free of adhesive.

In other embodiments, the disclosure relates to a two-component device as described above wherein the first and second flat flexible attaching members are perforated or sliced in a direction generally perpendicular to their respective wound edges thereby facilitating removal of a portion of the device thereby reducing the size of the device or creating multiple devices.

In other embodiments, the disclosure relates to a two-component device as described above wherein the device contains embedded infection indicators useful for detecting the development of infection.

In other embodiments, the disclosure relates to a two-component device as described above wherein the device is adapted for transdermal drug delivery.

In other embodiments, the disclosure relates to a two-component device as described above wherein the device comprises an elastic tension indicator element.

In other embodiments, the disclosure relates to a two-component device as described above wherein the first elongated component and the second elongated component, or elements thereof, are die cut from sheet stock.

In other embodiments, the disclosure relates to a two-component device as described above wherein the first and second elongated components are interlaced.

In other embodiments, the disclosure relates to a two-component device as described above wherein the first and second elongated components are mated in a keyhole arrangement.

In other embodiments, the disclosure relates to a two-component device as described above wherein the width of the attached portions is constant.

In other embodiments, the disclosure relates to a two-component device as described above wherein at least the first and second flat flexible attachment members are produced from colored or opaque stock.

In other embodiments, the disclosure relates to a two-component device as described above wherein the mechanical manipulation comprises the introduction of discontinuities selected from the group consisting of slices, perforations or punches.

In other embodiments, the disclosure relates to a two-component device as described above wherein the mechanical manipulations increase breathability of the material.

In other embodiments, the disclosure relates to a two-component device as described above wherein the mechanical manipulations facilitate transfer of sweat from the skin beneath the first and second flat flexible attaching members when in use.

In other embodiments, the disclosure relates to a two-component device as described above wherein the mechanical manipulations result in elastic-like properties.

In other embodiments, the disclosure relates to a two-component device as described above wherein the mechanical manipulation comprises the introduction of slits in flat flexible attaching members thereby creating a plurality of adhering subdomains.

DETAILED DESCRIPTION OF PREFERRED EMBODIMENTS

Figure 1:
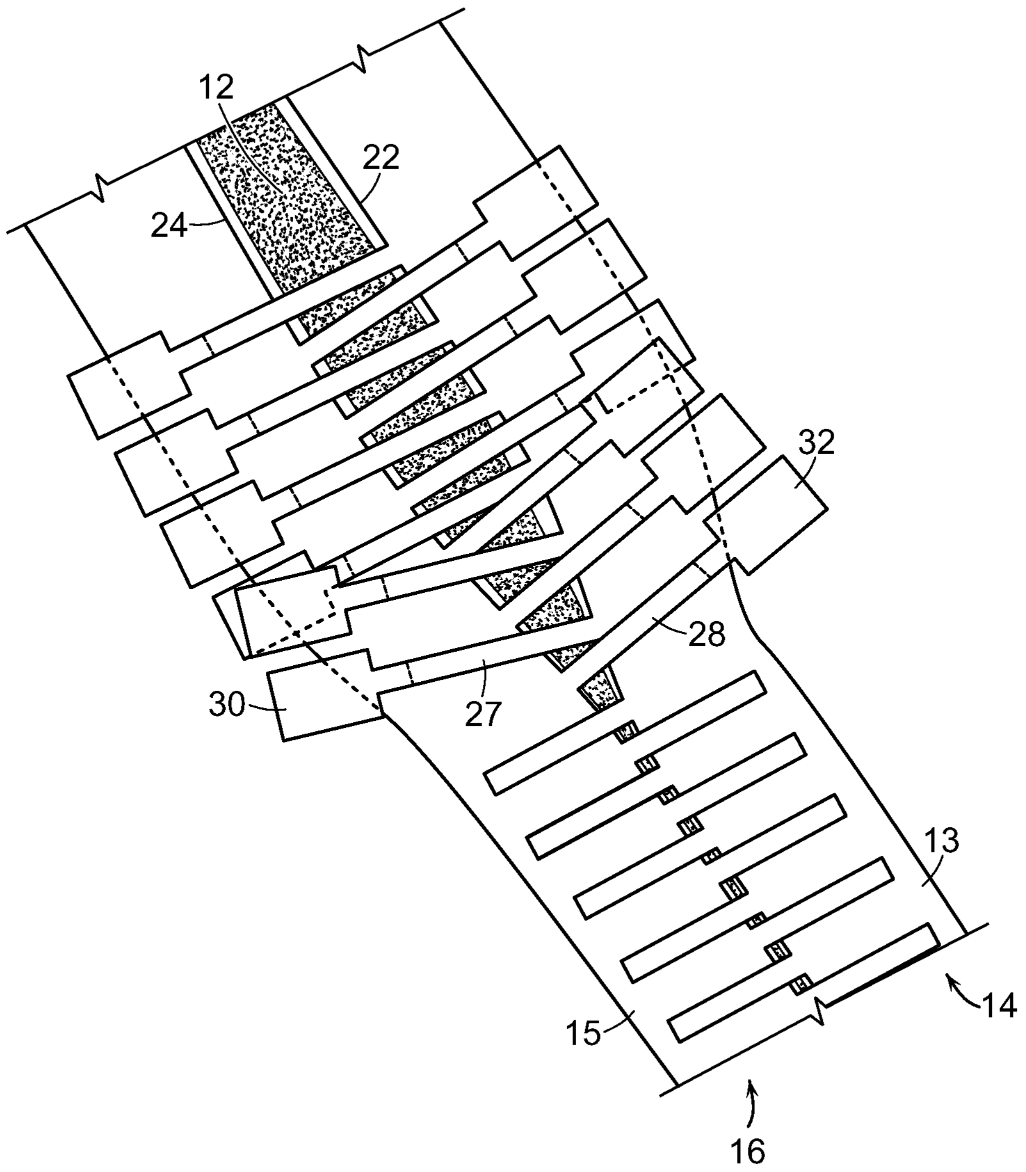
FIG. 1 is a perspective view of an embodiment of the closure device in which both components comprise a plurality of lateral translation elements, the view showing the closure device in a partially closed condition.

The present disclosure relates to a two-component device for closing a wound or incision. In embodiments, the device comprises a first elongated component. The first elongated component comprises a first flat flexible attaching member comprising a wound edge and a lower surface. The lower surface has an adhesive layer, the adhesive layer being protected by one or more release liners prior to application. The first elongated component also comprises one or more first lateral translation elements, each first lateral translation element comprising one or more first elongated connectors attached to a single first pulling element. The terms "flat flexible attaching member(s)" and "adhesive-backed anchoring member(s)" are used synonymously herein, as are the terms "attaching member(s)" and "anchoring members".

In addition to the first elongated component, the device comprises a second elongated component comprising a second flat flexible attaching member comprising a wound edge and a lower surface. The lower surface has an adhesive layer, the adhesive layer being protected by one or more release liners prior to application. The second elongated component comprises a plurality of second lateral translation elements, each second lateral translation element comprising one or more second elongated connectors attached to a single second pulling element.

The device further comprises a means for attaching the one or more first elongated connectors to the second flat flexible attaching member during closure, the attachment of the one or more first elongated connectors to the second flat flexible attaching member forming an attached portion and a bridging portion for each attached first elongated connector. The device further comprises a means for attaching the one or more second elongated connectors to the first flat flexible attaching member during closure, the attachment of the one or more second elongated connectors to the first flat flexible attaching member forming an attached portion and a bridging portion for each attached second elongated connector.

For purposes of illustration, the instances will now be described in detail with respect to four specific embodiments referred to as: 1) Zipper, 2) Keyhole A, 3) Keyhole B, and 4) Interlaced embodiments. Prior to describing these embodiments in detail, certain considerations common to all embodiments will be discussed.

Interlaced and Keyhole Embodiments

Embodiments of the medical device of the present disclosure can be interlaced or non-interlaced. Interlaced embodiments are those wherein both the first and second components comprise two or more elongated connectors, wherein the first and second elongated connectors of the first component are attached to a single pulling element and the first and second elongated connectors of the second component are attached to another single pulling element. Further, an elongated connector from one of the two components passes through the void formed between the two elongated connectors of the other component. When assembled in this manner, the first and second components are linked and they cannot be separated without cutting or breaking at least one of the two components. A simple analogy to such an interlaced device is a pair of interlocking rings.

One of skill in the art will recognize that more complex interlaced embodiments can be produced wherein, referring to a first component, interlacing extends to two or more adjacent voids formed by three or more adjacent elongated connectors. Examples of such embodiments are provided in the disclosures in issued US patents referenced and incorporated by reference in the Background section.

Interlaced embodiments can be produced in a variety of ways. Consider, for example, the simplest embodiment to which the analogy to interlocking rings has been made. To produce such an interlaced structure, the first and second components can be die cut as monolithic elements. One of the two components can then be cut, interlaced with the uncut component, and the cut can then be repaired, for example, with adhesive or some other appropriate means. As an alternative method for producing the simplest interlaced embodiment, one component can be die cut monolithically, and the second component can be die cut with an element, or a portion of an element missing. For example, the second component could be die cut with one of the two required elongated connectors being absent. The missing second elongated connector could be provided as a separate die cut element, complete with adhesive. Following interlacing of the first component with the partial second component, the interlaced structure could be completed by attaching the separately supplied missing elongated connector.

Neither of the interlaced device production methods discussed above is adaptable to a computer-controlled, mass production, manufacturing technique. Such methods have, however, been developed, publicly disclosed and incorporated herein by reference. Given this disclosure, one of skill in the art can develop and implement computer-controlled methods for production of interlaced embodiments of the two component medical device of the present disclosure.

A non-interlaced alternative design has been referred to as the "key-hole" design. In this design, for example, the two components of the two-component medical device are separately produced. In a preferred method, they are produced through a die cut process as monolithic components. Each of the two monolithic components comprise a flat flexible attaching member, elongated connector(s) and a pulling element. The elongated connector(s) of the first component are centrally located in the assembled and applied device. The elongated connectors of the second component are spaced apart thereby creating a void, or "key-hole" through which the pulling element and elongated connector(s) of the first element are inserted. Following insertion and rotation of the first and second components into a common plane, the two components are mated in a "key-hole" arrangement and the two-component device is in condition for application.

Sheet Stock

In preferred embodiments, the flat flexible attaching members, elongated connectors and pulling elements are produced from a substantially inelastic polymeric material. Alternatively, they may be produced from an elastic material which is reinforced with an inelastic structural component thereby rendering the device substantially inelastic. For example, such inelastic materials may include monofilament polymeric line or mesh. Such reinforced polymers are referred to herein as polymeric composites. A reinforcing, inelastic structural material is referred to in the art as "scrim". Scrim may be a woven textile or polymer, a non-woven polymer, or any other structural material that acts to stabilize the substrate. Preferably, the scrim reinforced substrate will have a high degree of permeability (e.g., 1,000 to 8,000 liters/sec/m$^2$).

Additionally, non-reinforced polymers exhibiting a degree of elasticity (e.g., polyurethane and polyester) may be used in the production of flat flexible attaching members for embodiments in which flat flexible attaching members and elongated connectors are produced separately, and subsequently attached to one another (i.e., non-monolithic embodiments). A preferred polymer for the production of the flat flexible attaching members is polyurethane having a thickness of 3-12 mils. Such a polymer is breathable and exhibits a degree of flexibility. If a non-reinforced elastic polymer is used to produce a flat flexible attaching member, it will be preferable to reinforce the upper surface of the wound edge with an inelastic element so that the wound edge remains substantially straight across the incision site during the closure process. Such an element is referred to herein as a "wound edge bar". One skilled in the art will recognize that a wide range of inelastic polymers, or even metals, can be utilized in the production of a wound edge bar for the purpose of providing rigidity to the wound edge. Vapor permeable polymeric materials that satisfy the other requirements for use in the manufacturing of the device offer improved comfort and are preferred. Transparent stock is also preferred so that the healing process and the entire wound site can be monitored easily. Therefore, at least the first and second flat flexible attachment members are produced from transparent stock in preferred embodiments. As an alternative design choice, colored or opaque stock may be used in the production of at least the first and second flat flexible attachment members when circumstances (e.g., cost considerations) dictate.

In preferred embodiments, the flat flexible attaching members, elongated connectors and pulling elements are produced from sheets or rolls of polymeric material or polymeric composite material such as polyurethane and polyester. The sheet or roll stock is typically referred to as "film" as the thickness in preferred embodiments ranges from about 0.5 mil to about 5 mil, and may vary depending upon application. Die cutting these elements from polymeric sheet stock to provide two monolithic components (i.e., having no seams or joints) which, when assembled/packaged comprise the two-component device, is a particularly cost-effective approach to manufacturing. Die cutting can be combined with other assembly steps, for example, in connection with the production of interlaced embodiments as discussed elsewhere herein. Laser and ultrasonic trimming devices are also examples of equipment that can be used to cut the components of the present disclosure. The sheet stock may be perforated to allow for the exchange of air with the skin beneath the two-component device.

Mechanical Manipulation of Sheet Stock

The subject disclosure relates to improvements and modifications in polymeric films that comprise the flat flexible attaching members of the two-component medical devices. More particularly, instances of the present disclosure include a first and second flat flexible attaching member characterized by the presence of one or more discontinuities in the polymeric film allowing for the release of sweat from beneath the first and second flat flexible attaching members. The use of an inherently breathable polymeric film (i.e., a polymeric film, that without any mechanical manipulation, allows for the exchange of air with the skin beneath the first and second flat flexible attaching members) for the production of the first and second flat flexible attaching members does not allow for the release of sweat.

Certain mechanical manipulation of an inherently breathable polymeric film that does not allow for the release of sweat will permit sweat to pass from the skin beneath the wound closure device. The same can be said for mechanical manipulation of a polymeric film that is not inherently breathable.

The introduction of discontinuities that do allow for the release of sweat from beneath the first and second flat flexible attaching members addresses the problem of adhesion loss. There is variability in the size, number and distribution of active sweat glands in humans. For example, according to one expert estimate, the palm of the hand has about 370 sweat glands per cm$^2$. By comparison, the back of the hand has about 200; the forehead has about 175; the breast, abdomen and forearm have about 155; and the leg and back have about 60-80 (all expressed in sweat glands per cm$^2$). Given this sweat gland distribution pattern, one skilled in the art will recognize that discontinuities should be introduced broadly, across the area of the flat flexible attaching members, to be most effective in addressing the problem of adhesion loss.

Discontinuities can be introduced into the polymeric material used to produce the first and second flat flexible attaching members in a variety of ways. It is not a requirement that all discontinuities introduced into a particular flat flexible attaching member be homogenous or uniform. Die cutting technology is a preferred method for the introduction of discontinuities. Die cutting is a process involving the use of a die to shear a web or webs of low-strength materials such as polymeric sheet materials. For example, a needle or pin die could be used to introduce hundreds, or even thousands, of small, round discontinuities into the first and second flat flexible attaching members through a perforation process. Perforation, as used herein, refers to a process wherein a discrete piercing element, such as a pin in an array of pins assembled on a die, penetrates a material leaving no excess material on either side (e.g., entry or exit side). Whether penetration by a particular piercing element leaves excess material on one side or another (e.g., deformation of material on the exit side) depends not solely on the piercing element, but also the material being pierced (in this case a polymeric sheet material). For example, a larger gauge piercing element, the size of a small nail, for example, may create exit deformation in some polymeric sheet stocks that would not be useful for the introduction of discontinuities consistent with the present disclosure. The shape of a piercing element need not be round. There are no geometric restrictions on the shape of a piercing element.

For the introduction of larger discontinuities, like those produced by piercing a polymeric material with a small nail, a punch process may be more appropriate. A punch, as used herein, is contrasted from a perforation by the requirement that material is removed in a punch process. For example, a punch die of a particular diameter would punch, or remove, a chad from the polymeric material. Such loose chads are removed in a variety of ways in a die cutting process including, for example, inclusion of an adhesive web to capture cut chads, or a vacuum process.

In addition to perforation or punching, as described above, cutting (e.g., die cutting) can be used to introduce one or more slits or slices into the flat flexible attaching members. Again, in view of the sweat gland distribution discussed above, a plurality of slits will be preferred.

One of skill in the art will recognize that a certain amount of routine experimentation may be required to optimize discontinuity size, shape and distribution. Certain larger gauge perforations, punches or slits will allow for the transfer of sweat from the skin beneath the wound closure device. Certain smaller gauge perforations, produced for example using a pin die as discussed above, may allow for vapor transfer but not sweat transfer. It is a matter of routine experimentation to determine discontinuity parameters that will allow for sweat transfer. Optimal discontinuity design for one specific polymer sheet, backed with one specific adhesive, may not work well using a different polymer sheet and/or different adhesive. A particularly soft or gummy adhesive, for example, may function in a self-healing role by flowing in to fill perforations when such perforations are introduced with a particularly small diameter piercing element.

It will also be recognized by one of skill in the art that punch-type discontinuities will tend to remove skin contact surface area (and adhesive) from a flat flexible attaching member. For this reason, larger punch-type discontinuities (e.g., paper punch size discontinuities, or larger) are not favored, at least for applications requiring high adhesion characteristics.

For a variety of reasons, slits or slices introduced into the flat flexible attaching members are preferred. For one, like perforations, slits or slices do not remove material from the flat flexible attaching members and, therefore, the flat flexible attaching members retain their full surface area and adhesive content following the introduction of the slits or slices. Slits or slices can be straight or curvilinear and the slits or slices can be relatively long (e.g. running the length or width of a flat flexible attaching member) or generally short in length. Furthermore, under flexion, a slit or slice will tend to open up. This tendency serves at least two purposes that represent advantages in the context of a two-component wound closure device. First, the "opening up" of a slit or slice under flexion enables relative unimpeded transfer of sweat from the surface of the skin beneath the flat flexible attaching member to the external environment. Second, the "opening up" of the slit or slice tends to allow the adhesive-backed surfaces adjacent to the slit or slice to remain in good adherence with the skin. The presence of the slit or slice tends to reduce peel or shear forces that tend to result in poor adherence characteristics.

In preferred instances, slits are introduced into each flat flexible attaching members in a direction generally perpendicular to the wound edge of the flat flexible attaching member. The slits are positioned so that they will fall between elongated connectors in an applied device. Slits oriented in this way tend to allow a particular flat flexible attaching member to be viewed as a unit having a number of adhering subdomains, with the adhering subdomains being divided by the introduced slits. The adhered two-component device opens in an accordion-like manner under flexion. In instances of the two-component device disclosed, the adhering subdomains can actually separate from one another over time thereby creating independent subdomains.

Mechanical manipulation of the type described above can provide for "elastic-like" properties in non-elastic polymers. Although the mechanical manipulation does not change the non-elastic characteristic of the particular polymer, the introduction of voids or discontinuities can allow for movement or dimensional flexion when compared to an otherwise identical polymer lacking voids or discontinuities.

Application Considerations

The use of the device to close a laceration or incision will be discussed in greater detail below, however, a brief orientation at this stage in the discussion is helpful. In use, the adhesive-backed attaching member of the first component of the device is applied to the skin of the animal or human patient adjacent to the laceration or incision to be closed. The wound edge of the first component is placed very near to the edge of the laceration or incision, but not so close as to introduce adhesive from the first component attaching member into the open area of the laceration or incision. The one or more elongated connectors extend from the wound edge of the attaching member of the first component, in a direction which is generally perpendicular to the wound edge, and extend across the area of a laceration or incision to the opposite side of the laceration.

A similar application procedure is followed for application of the second component, the procedure for the application of the second being the mirror image of the procedure for application of the first. Following application of the flat flexible attaching members, the laceration is closed by either pushing attaching members toward one another, or by pulling them together by grasping one or more elongated connectors from each component and pulling the laceration closed. Very fine adjustment can be made in the X and Y dimension ensuring laceration closure with minimal scarring. When the first and second component are positioned to the satisfaction of the physician, or other individual applying the device, the relationship of the two components is fixed by attaching the one or more elongated connectors of the first component to the attaching member of the second component, and by attaching the one or more second elongated connectors of the second component to the attaching member of the first component.

Adhesives

The adhesives selected for use in connection with the present disclosure must meet a number of requirements. First, adhesive which is to come into contact with the skin must be selected to minimize the potential for adverse reaction by the skin. That is, the adhesive selected should be hypoallergenic. Additionally, all adhesives, whether or not they are intended to contact the skin, must provide a secure hold for a period of time sufficient for the healing process to progress to the point where removal of the device is appropriate. An adhesive hold period of about 7-10 days is generally suitable.

Adhesive is a preferred means of attaching one or more elongated connectors to a flat flexible attaching member. In one embodiment, adhesive is applied to at least a portion of the lower surface of the elongated connectors for attaching the elongated connectors of one of the two components to the applied attaching member of the other component. Alternatively, or additionally, adhesive may be applied to a portion of the upper surfaces of the first and second flat flexible attaching members. Release liners are used to protect applied adhesives prior to application of the device.

The elongated connectors have two parts or portions, an attached portion and a bridging portion. The attached portion of the elongated connectors, as the name indicates, is that portion which is attached to the attaching member of the opposing component following application of the device. The bridging portion is the portion of the elongated connector or members which spans the over-laceration area. In further refined embodiments, the lower surface of the bridging portion contains less adhesive than the attached portion. In preferred embodiments, the entire bridging portion of the one or more elongated connectors is free of adhesive or, alternately, have adhesive but this is blocked with another film (kill layer) to render the adhesive in the bridging portion nonfunctional.

Elongated Connectors

As mentioned above, the dimension of the elongated connectors is strap-like in that their width is substantially greater than their thickness. In light of the fact that the point of attachment between the first and second elongated components is between the under-side of attached portions of elongated connectors with the upper surface of attached elongated components, maximizing the area of contact will result in a more secure closure of the device because the area of adhesive contact is maximized. Thus, from the standpoint of security of closure, wider attached portions are preferred. However, as the width of all the elongated connectors is increased, the distance between elongated connectors necessarily is decreased. It is extremely important that there be enough distance between adjacent elongated connectors to facilitate fine adjustment of the device as the second attaching member is being positioned, and after the two attaching members are positioned, but prior to fixing their relationship by attaching elongated connectors to attaching members.

As was stated in U.S. Pat. No. 6,329,564, the disclosure of which is incorporated herein by reference: There is no absolute minimum which can be stated with respect to spacing between elongated connectors. Preferred ranges are probably best stated as a percentage of device length (i.e., the dimension of the device generally parallel the laceration or incision). For example, a spacing of between about 5% to about 10% of the bandage length is an example of an appropriate range.

This spacing provides substantial adhesive contact between attached portions of elongated connectors with attaching members, as well as sufficient spacing for fine adjustment of both before and following the attachment of the second attaching member. Fine adjustment made after the attachment of the second attaching member is generally a concern after the laceration has been closed and just prior to attachment of elongated connectors to a flat flexible attachment member. At this stage in the application process, the bridging portions of the one or more first elongated connectors and the bridging portions of the one or more second elongated connectors are aligned with one another over the closed laceration or incision. In a preferred embodiment of the present disclosure, the average width of the bridging portions is less than the average width of the attached portions of the elongated connectors. Average width is determined by measuring from the outer perimeters of the bridging portions and the outer perimeters of the attached portions.

This difference in width in the bridging portion relative to the attached portion affords advantages over prior art devices in which the width of elongated connectors was substantially constant along their length. Consider, for example, a prior art device designed for maximum security. In such a device, the elongated connectors would be placed as close as possible, while still providing for a minimum acceptable degree of adjustment range. If the bridging area were narrowed in such a device, the net effect would be an increase in exposed area over the laceration (which is desirable for application of medicines, removal of exudates, etc), as well as an increase in the range of adjustment (narrowing the width of the elongated connectors in the bridging portion effectively increases the distance between adjacent bridging portions).

Considering the same prior art device discussed in the preceding paragraph, holding the width of bridging portion constant, while increasing the width of the attached portions provides for greater security as the area of adhesive contact is effectively increased. It will be recognized by one skilled in the art that hybrid configurations (i.e., devices having narrowed bridging portions and widened attached portions relative to prior art, uniform width devices) represent important embodiments of the present disclosure.

Elongated connectors may be viewed as strap-like in their dimensions. In preferred embodiments, a portion of the elongated connectors is cut away to increase the unobstructed surface area over the wound or incision. This tends to facilitate drainage of exudates and application of medication. This cut-out is best produced during the die cut process. U.S. Pat. No. 6,329,564, the disclosure of which is incorporated herein by reference, depicts cut-outs, for example, in FIG. 3. The shape of the cut-out is not critical. What is important is that the structural integrity of the elongated connectors is not compromised by the introduction of the cut-outs.

Pulling Elements

Preferred embodiments of the present disclosure include pulling elements which are attached to elongated connectors, or to extensions of elongated connectors. Extensions of elongated connectors could themselves be considered to be pulling elements in embodiments in which only one elongated connector is associated with a component. By definition, the attached portion of an elongated connector attaches to the attaching member of another component. Extensions of an elongated connector extend the length of the elongated connector for ease of application, and are generally removed following the application process. Perforations or scoring are preferably provided to facilitate their removal. For embodiments in which the number of elongated connectors associated with a component is greater than one, a pulling element is useful for joining the elongated connectors or extensions of elongated connectors to enable a user to easily apply a pulling force to more than one connecting member.

Removal of the pulling elements minimizes the footprint of the applied two-component device. This decrease in the overall size of the device reduces the chance that a portion of the bandage may be caught, for example, on clothing or a pillow. Such an occurrence could tend to pull the applied device away from the skin thereby causing the wound or incision to open. Minimizing the overall footprint of the applied device also tends to provide for a more comfortable fit.

Eversion Edges

In preferred embodiments, the wound edges of the first and second flat flexible attaching members, are adapted to evert (or raise) skin edges to promote wound healing. It is known in the art that everting, raising or mounding of the skin edges at the wound or incision site prevents wound inversion. One way in which this can be accomplished is to provide a bend at the wound edge. The bend may be angled or arcuate. The adhesive on the lower portion of the flat flexible attaching members is also applied to the wound edge portion. When attached to the skin this eversion edge tends to lift the edges of the skin at the point of closure contact, thereby promoting wound or incision healing.

Coding

To minimize confusion for new users of the device of the present disclosure, the pulling elements and attaching members may be coded to enable user distinction. Thus, for example, the coding may comprise an observable geometric distinction between the shape of the pulling elements and the shape of the flat flexible attachment members. In another embodiment, such coding may comprise printed indicia to enable user distinction between the components. Colors may also be used to provide this distinguishing function.

Lateral Translation Element

Lateral translation elements, as described herein, each comprise one or more elongated connectors attached to a single pulling element. As will be exemplified in connection with four specific embodiments of the present disclosure, each lateral translation element is selected from the group consisting of: a) a single elongated connector and a single pulling element; and b) a plurality of elongated connectors and a single pulling element.

Release Liners

The adhesive-backed surfaces of the device of the present disclosure are protected (e.g., from contamination and oxidation) by the application of release liners during the manufacturing process. In some instances, multiple release liners, or release liner systems may be used to protect a single, uninterrupted, adhesive-backed surface. Consider, for example, the attaching members of the disclosed device. In order to precisely attach the wound edge of an attaching member adjacent a laceration or incision to be closed, it is preferable to hold the attaching member with one hand leaving the other hand free to manipulate the laceration or incision area. Thus, a plurality of release liners on each attaching member is preferred. In preferred embodiments, a first release liner, which protects the wound edge, is removed first during the application process. In this way, a portion of the wound edge can be adhered to the skin while leaving a protected portion of the attaching member which can be held (e.g., in a gloved hand) without the device adhering to the fingers of the user. Once the wound edge has been applied, the second release liner can be removed to fully secure the attaching member Preferred material for use in production of release liners includes paper, cardboard or polymeric sheet material, for example. The use of a plurality of release liners in connection with the adhesive associated with the elongated connectors is less important as extensions of the elongated connectors and pulling elements are provided "adhesive-free" in preferred embodiments. To minimize confusion for new users of the device of the present disclosure, the release liners may also be coded. Release liner colors or printed indicia on the release liner are examples of coding enabling a user to readily identify the order of release liner removal.

As discussed above, the film or sheet stock used to manufacture the first and second components of the device of the present disclosure can be, and preferably are, extremely thin. When applying an attaching member produced from such thin stock next to a laceration or incision, it is easy to imagine difficulties associated with wrinkling and overlapping of edges, inadvertent or incorrectly positioned initial contact, etc. The release liners employed in connection with the device can provide substantial aid in working with the device, particularly a device produced from thin sheet stock, if properly selected. For example, if two release liners are used to protect the adhesive-backed surface of an attaching member, the characteristics of the release liner protecting the wound edge of the attaching member is far less important than the characteristics of the later-removed, second release liner protecting the flat flexible attaching member. If, for example, a semi-rigid second release liner is employed, this will enable more precise placement of the wound edge of the flat flexible attachment member.

Alternative Stock

The embodiments of the device discussed above comprise first and second components which are monolithic in nature. That is, the first component (which includes an attaching member and one or more elongated connectors) is produced from a single sheet of stock material without joints or seams. The same statement applies to the second component. In an alternative embodiment, the first and second components are not monolithic in nature. This alternative embodiment is based on the recognition that the desired physical properties of the attaching members and the elongated connectors are not, in every instance, identical. For example, a degree of elasticity is a desirable feature in an attaching member when applied, for example, to an area such as a joint. An attaching member produced from a film having a degree of elasticity is less likely to release prematurely than an attaching member produced from a substantially inelastic material when applied to such an area. Elasticity is a property to be avoided when producing elongated connectors. Any stretching of elongated connectors is to be avoided as this will tend to allow premature opening of a laceration or incision.

In embodiments in which the first and second components are not monolithic, attaching members may be produced from stock having a degree of elasticity. Elongated connectors are produced separately from stock which is substantially inelastic. One or more first elongated connectors are then attached (e.g., with adhesive) to a first attaching member to produce a first component. A second component is similarly constructed. As discussed elsewhere, a wound edge bar may be attached to reinforce the wound edge, particularly in embodiments wherein the sheet stock employed has a degree of elasticity.

It is not a requirement that elongated connectors and attaching members of non-monolithic components be produced from different stock material. It may be desirable, for example, to create an overlap in a portion of the elongated connectors (e.g., the bridging portion) in order to provide for additional strength. Thus, double-thickness in the bridging area may be provided by producing a monolithic attaching member including a portion of connecting member. A separately produced elongated connector is then attached, in an overlapping manner, to the monolithic attachment member. This creates a first component which is double-thick in the bridging portion for additional strength and further eliminates stretching.

Reinforcing Elements

It may be desirable to reinforce the wound edge portion of the attaching member with another layer of less flexible stock. This "wound edge bar" would provide better translation of the force applied by the elongated connectors uniformly along the entire wound edge. Similarly, it may be desirable to reinforce the optional pulling element, or a portion thereof, with another layer of less flexible stock. This "pull bar" would be useful in applying uniform tension from the pulling element to all elongated connectors, as the device is positioned for closure. This feature would become more important in embodiments of the device intended to close long lacerations or incisions where there might be up to four or more elongated connectors to be pulled and secured to each flat flexible attachment member.

Elastic Tension Indicators

The bandage of the present disclosure may optionally include an elastic tension indicator element. The purpose of the tension indicator element is to provide a visual indication that a desired tension has been reached while applying the bandage. For example, materials are known in the art which change color when a predetermined tension is applied. Similarly, other graphic representations may be used for this purpose. For example, a rectangular graphic representation may be applied to an elastic tension indicator element. As this tension indicator is stretched, the graphic representation of the rectangle stretches. This element may be designed such that the desired tension is indicated when the original rectangular representation is stretched to the point where it closely approximates a geometric square.

It is desirable that this elastic tension indicator element be removable with the pulling elements following application of the bandage. At a minimum, the elastic tension indicator element should be positioned in the bandage such that when the bandage is applied, it is not possible for the elastic element to continue to stretch and release the desired tension previously established.

Transdermal Drug Delivery

The two-component device of the present disclosure can be optionally adapted for transdermal drug delivery. As is known in the art, a drug is deliverable transdermally through the skin. For such an application, a drug-containing patch is secured to at least one of the flat flexible attaching members in such a way that the drug can be delivered through the skin. Given the fact that there will be no adhesive contact between the skin and the flat flexible attaching member in the area of the drug delivery patch, it may be necessary to increase the size of the flat flexible component to secure the bandage in such a transdermal drug delivery embodiment. Transdermal drug delivery is well known in the art and a review of the background is not necessary to enable one of skill in the art to make and use the presently disclosed instances.

Embedded Infection Indicators

The use of embedded infection indicators represents a relatively new technology that can be incorporated to provide for a wound closure device that can, for example, change color as an indication of the presence of unwanted bacteria. One technology utilizes the release of a fluorescent dye from nanocapsules, the release being triggered by toxins secreted by the unwanted bacteria.

Methods of Use

The present disclosure also relates to methods for closing a laceration or incision using a device of the type described above. Such methods include the steps of applying the attaching member of a first and second component on opposing sides of a laceration or incision to be closed. The laceration is then closed by the user either by pushing the edges of the laceration together by manipulating the skin in the area of the flat flexible attaching members, by pulling the laceration closed using lateral translation elements, or by some combination thereof. Once the laceration is closed, the position of the first and second component relative to each other is fixed by attaching the elongated connectors to the flat flexible attaching members.

Having discussed above considerations common to all embodiments, following is a description of four specific embodiments referred to as: 1) Zipper, 2) Keyhole A, 3) Keyhole B, and 4) Interlaced embodiments.

1) Zipper

The Zipper embodiment is shown in FIG. 1. In FIG. 1 a Zipper embodiment of the present disclosure is shown in use for the closure of an incision 12. The first elongated component 14 and second elongated component 16 are shown in cooperative engagement drawing the opposed edges of the incision 12 together for the purpose of establishing closure and healing with optimal cosmetic results.

Figure 2:
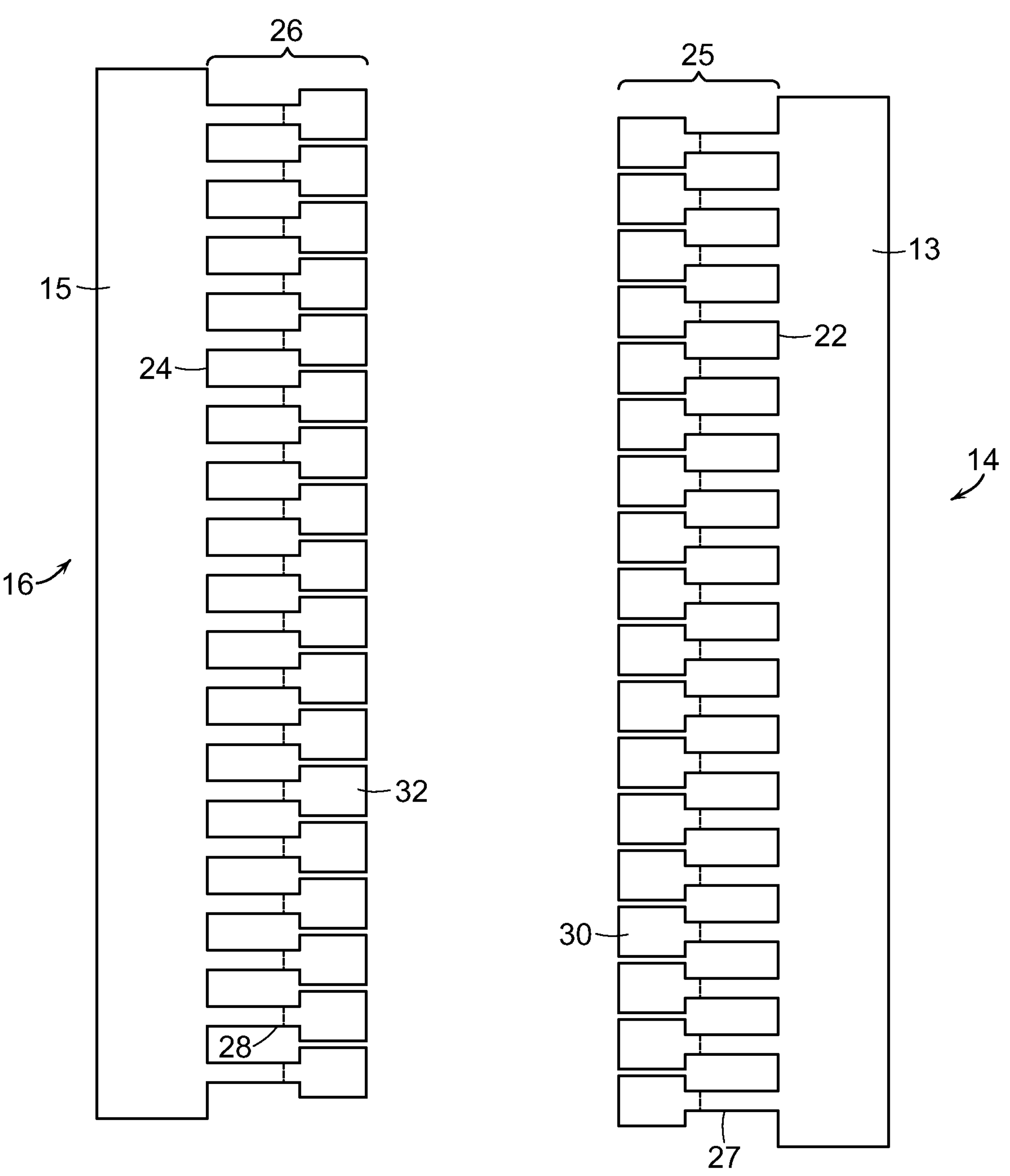
FIG. 2 is a top view of an unapplied two-component embodiment of the present disclosure wherein both components comprise a plurality of lateral translation elements.

To facilitate clear reference to the features of the first and second elongated components of the Zipper embodiment of the present disclosure, FIG. 2 shows separated views of the first and second elongated components 14 and 16. The first elongated component 14 comprises a first flat flexible attaching member 13 with an adhesive layer (not shown) provided on the lower surface of the first flat flexible attaching member 13. The second elongated component 16 comprises a second flat flexible attaching member 15 with an adhesive layer (not shown) provided on the lower surface of the second flat flexible attaching member 15. Prior to application of the elements of the two-component device, the adhesive layer of the flexible attaching members 13 and 15 are protected by release liners which are discussed in greater detail above. In use, the release liner(s) protecting the adhesive layer on first flat flexible attaching member 13 are removed and the first wound edge 22 of the first flat flexible attaching member is aligned with one edge of the incision to be to be closed. In many surgical procedures, the incision made is generally straight, as are the wound edges 22 (first) and 24 (second) shown in FIG. 2.

Referring specifically to the first elongated component 14, and second elongated component 16, as shown in FIG. 2, additional elements include a plurality of first lateral translation elements 25 and a plurality of second lateral translation elements 26. In the Zipper embodiment, each lateral translation element 25 (first) and 26 (second) comprises a single first elongated connector (27 (first) or 28 (second)) attached to a single pulling element (30 (first) or 32 (second)).

As mentioned previously, in many embodiments one of the first or the second elongated component, but not both, comprise one or more lateral translation elements. In these embodiments, one of the first or the second elongated components comprises one or more lateral translation elements, and the other elongated component comprises a plurality of lateral translation elements, each comprising one or more elongated connectors attached to a single first pulling element. The existence of a plurality of lateral translation elements provides for the ability to maintain fine control over wound edge alignment over the full length of an extended wound closure device.

2) Keyhole A

Figure 3:
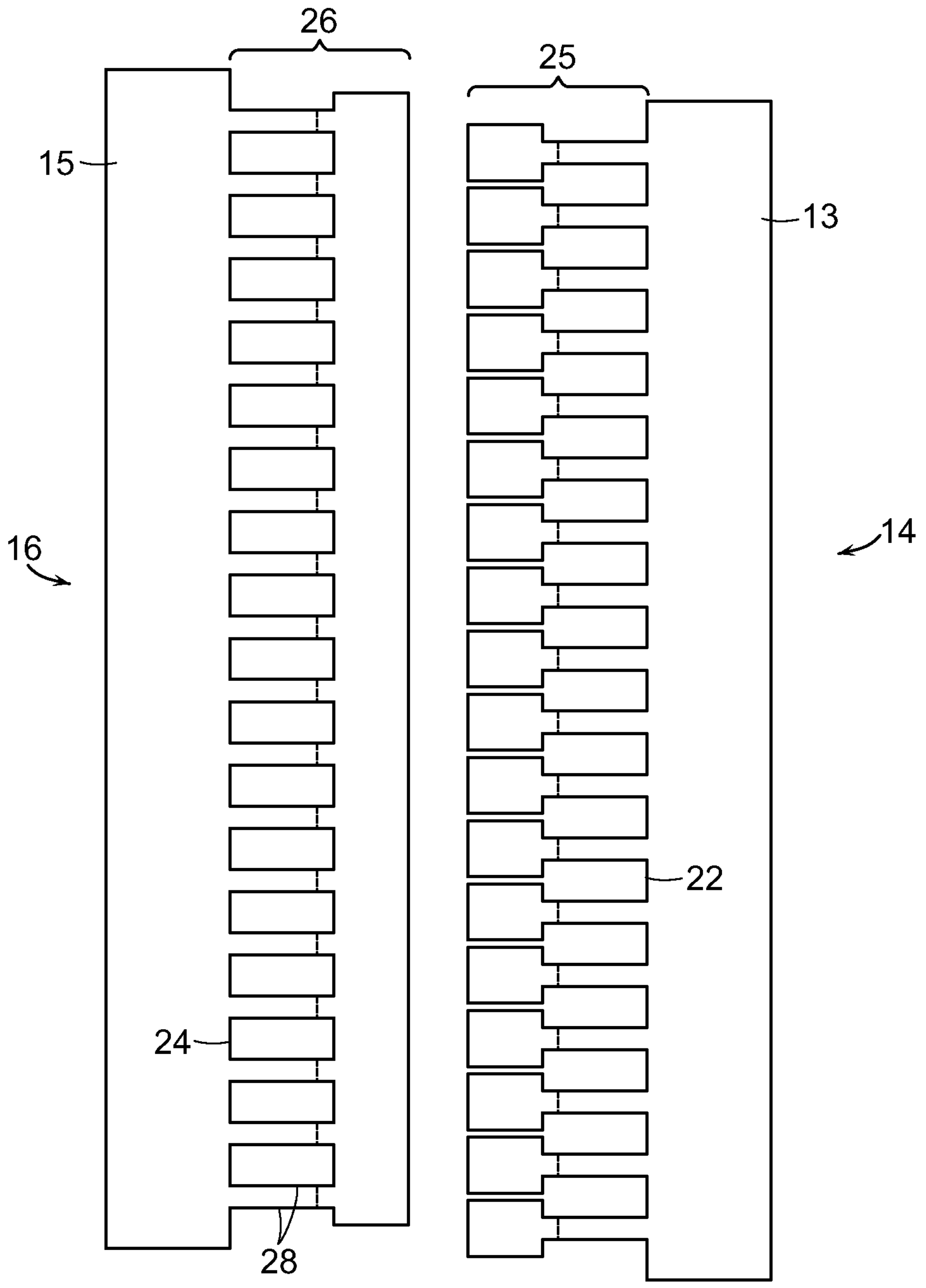
FIG. 3 is a top view of an unapplied two-component embodiment of the present disclosure wherein only one of the components comprise a plurality of lateral translation elements.

The Keyhole A embodiment is shown in FIG. 3. An effort has been made to retain common reference numerals between preferred embodiments to the extent that counterpart structures exist between embodiments. FIG. 3 is analogous to FIG. 2 in that it shows separated views of the first and second elongated components 14 and 16.

The first elongated component 14 comprises a first flat flexible attaching member 13 with an adhesive layer (not shown) provided on the lower surface of the first flat flexible attaching member 13. The second elongated component 16 comprises a second flat flexible attaching member 15 with an adhesive layer (not shown) provided on the lower surface of the second flat flexible attaching member 15. Prior to application of the elements of the two-component device, the adhesive layer of the flexible attaching members 13 and 15 are protected by release liners which are discussed in greater detail above. In use, the release liner(s) protecting the adhesive layer on first flat flexible attaching member 13 are removed and the first wound edge 22 of the first flat flexible attaching member is aligned with one edge of the incision to be to be closed. In many surgical procedures, the incision made is generally straight, as are the wound edges 22 (first) and 24 (second) shown in FIG. 2.

The differences between the Zipper embodiment and the Keyhole A embodiment are readily identifiable through a comparison of FIGS. 2 and 3. In both embodiments, one of the first or the second elongated components comprises one or more lateral translation elements, and the other elongated component comprises a plurality of lateral translation elements, each comprising one or more elongated connectors attached to a single first pulling element. In the Zipper embodiment, both the first and second elongated components comprise a plurality of lateral translation elements. In the Keyhole A embodiment, on the other hand, the first elongated connector 14 comprises a plurality of lateral translation elements 25, whereas the second elongated connector 16 comprises only a single lateral translation element 26.

Describing the Keyhole A embodiment in use, the individual lateral translation elements 25 of the first elongated connector 14 are threaded through alternating spaces between second elongated connectors 28 of the second elongated component 16 and the device is used to draw the wound edges of an incision together. One skilled in the art will recognize that it is immaterial whether the first elongated component 14 or the second elongated component 16 of the Keyhole A embodiment comprises the plurality of lateral translation elements. In other words, the mirror image of FIG. 3 also represents a Keyhole A embodiment.

3) Keyhole B

Figure 4:
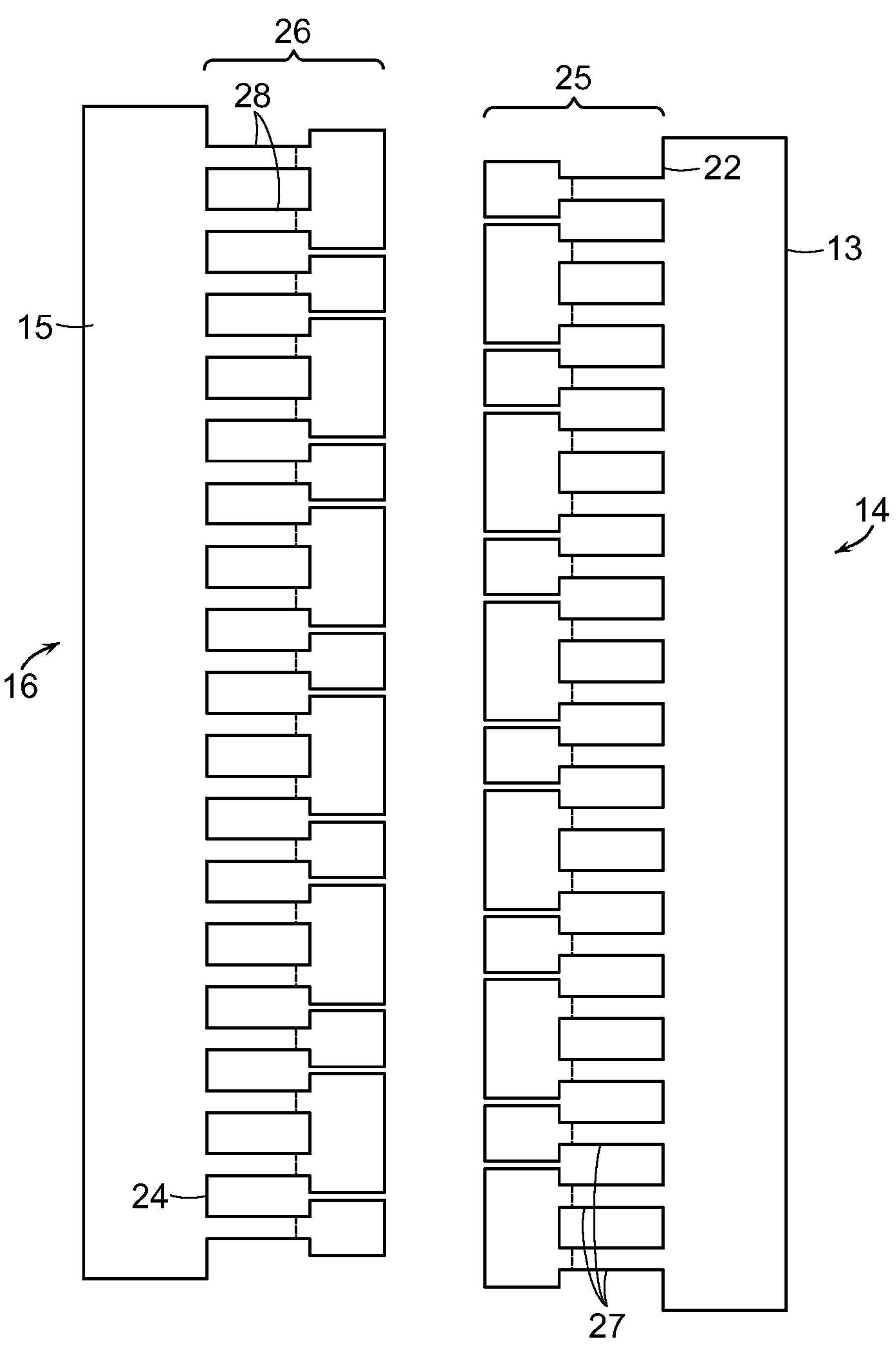
FIG. 4 is a top view of an unapplied two-component embodiment of the present disclosure wherein both components comprise a plurality of lateral translation elements.

The Keyhole B embodiment is shown in FIG. 4. An effort has been made to retain common reference numerals between preferred embodiments to the extent that counterpart structures exist between embodiments. FIG. 4 is analogous to FIGS. 2 and 3 in that it shows separated views of the first and second elongated components 14 and 16.

The first elongated component 14 comprises a first flat flexible attaching member 13 with an adhesive layer (not shown) provided on the lower surface of the first flat flexible attaching member 13. The second elongated component 16 comprises a second flat flexible attaching member 15 with an adhesive layer (not shown) provided on the lower surface of the second flat flexible attaching member 15. Prior to application of the elements of the two-component device, the adhesive layer of the flexible attaching members 13 and 15 are protected by release liners which are discussed in greater detail above. In use, the release liner(s) protecting the adhesive layer on first flat flexible attaching member 13 are removed and the first wound edge 22 of the first flat flexible attaching member is aligned with one edge of the incision to be to be closed. In many surgical procedures, the incision made is generally straight, as are the wound edges 22 (first) and 24 (second) shown in FIGS. 2-4.

The differences between the Keyhole A and Keyhole B embodiments are readily identifiable through a comparison of FIGS. 3 and 4. In both the Keyhole A and Keyhole B embodiments, one of the first or the second elongated components comprises one or more lateral translation elements, and the other elongated component comprises a plurality of lateral translation elements, each comprising one or more elongated connectors attached to a single first pulling element. In fact, in the Keyhole B embodiment, both the first 14 and second 16 elongated components comprise a plurality of lateral translation elements, each comprising one or more elongated connectors attached to a single first pulling element. First lateral translation elements are shown as 25 in FIG. 4 and second lateral translation elements are shown as 26 in FIG. 4.

Describing the Keyhole B embodiment in use, the individual lateral translation elements 25 of the first elongated component 14 alternate between lateral translation elements comprising a single first elongated connector 27 and two first elongated connectors 27. The design of the second elongated component 16 is similar to that of the first elongated component 14 in that it also comprises of plurality of lateral translation elements 26 alternating between lateral translation elements comprising a single second elongated connector 28 and two second elongated connectors 28.

With regard to the Keyhole B embodiment in use, the first 14 and second 16 elongated components are arranged such that lateral translation elements on opposing sides of the incision can be mated. In other words, lateral translation elements 25 of the first elongated component 14 comprising a single first elongated connector 27 align, across the incision, with a lateral translation element 26 of the second elongated component 16 having two second elongated connectors 28. The single lateral translation element 25 of the first elongated component 14 is threaded through the adjacent second elongated connectors 28 of the second lateral translation element 26 of the second elongated component 16. This threading and attachment procedure is followed to close the incision.

4) Interlaced

In the other preferred embodiments discussed above (Zipper, Keyhole A and Keyhole B), lateral translation elements associated with either the first elongated component 14, the second elongated component 16, or both, included lateral translation elements comprising a single first 27 elongated connector, second 28 elongated connector, or both (in the case of the Zipper embodiment). The manufacturing of the Zipper, Keyhole A and Keyhole B is straight-forward in that the first elongated component 14 and the second elongated component 16 are, in preferred manufacturing processes, simply die cut.

Figure 5:
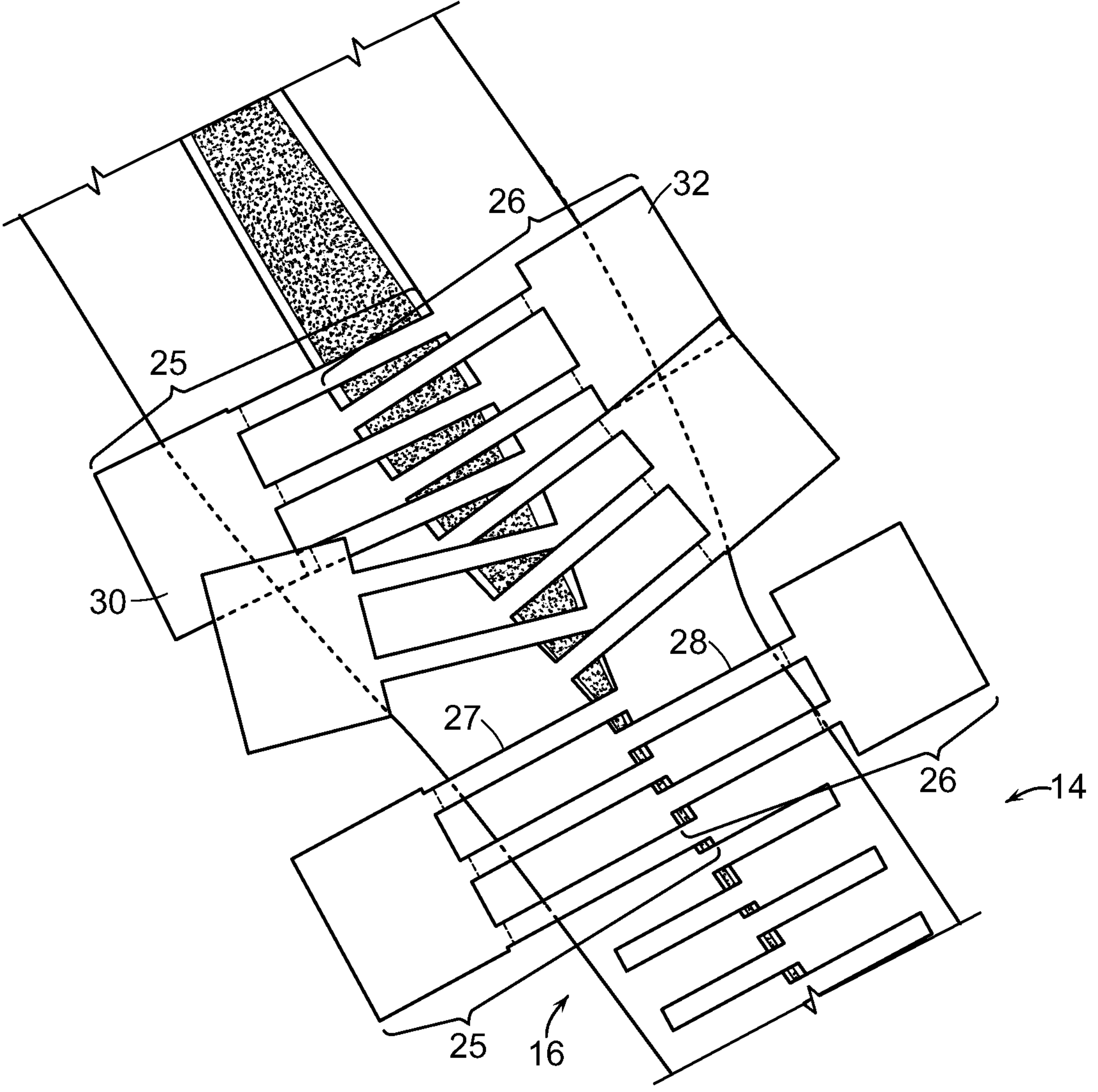
FIG. 5 is a perspective view of an alternative embodiment of the closure device in which both components comprise a plurality of lateral translation elements, the view showing the closure device in a partially closed condition.

The Interlaced embodiment is a more complex design requiring special manufacturing considerations. An example of an Interlaced embodiment is shown in FIG. 5. As can be seen in FIG. 5 first elongated component 14 and second elongated component 16 are each comprised of a plurality of lateral translation elements (first 25 and second 26). Each of the plurality of lateral translation elements (first 25 and second 26) are comprised of a plurality of first 27 and second 28 elongated connectors joined to a single first 30 or second 32 pulling element. It will be apparent to one skilled in the art that the first elongated component 14 and the second elongated component 16 of the Interlaced embodiment, cannot be independently die cut and later assembled for use as a wound closure device. The reason that this cannot be done is that the pulling elements (first 30 and second 32) block the interleaving of opposing first 27 and second 28 elongated connectors.

From a manufacturing standpoint, there are two alternatives to simple die cut processes of assembling an Interlaced embodiment. In one alternative, a two-step die cut process is employed wherein the first step comprises die cutting the first elongated component 14 without the associated pulling elements 25, and the second elongated component 16 without the associated pulling elements 26. The first 14 and second 16 elongated components die cut according to this paragraph (i.e., without pulling elements) can then be interleaved with alternating first 27 and second 28 elongated connectors. Separately provided pulling elements, first 30 and second 32, can then be attached to appropriate elongated connectors to produce the completed device via a two-step assembly process (manual or automated).

The second alternative to simple die cut processes is described in U.S. Pat. No. 7,332,641 which is incorporated herein by reference. Using the teachings of U.S. Pat. No. 7,332,641 one skilled in the art could produce the Interlaced embodiment as shown, for example, in FIG. 5, without the need for the two-step process described in the preceding paragraph.

The Interlaced embodiment as shown in FIG. 5 depicts lateral translation elements on one elongated component (either the first 14 or the second 16) having two elongated connectors (either the first 27 or second 28) mating across the incision with a lateral translation element from the other elongated component (either the second 16 or the first 14) having three elongated connectors (either the second 28 or the first 27). This lateral translation element mating arrangement can be referred to as the “2×3” embodiment, referring to the number of elongated connectors contributed by each participating lateral translation element pair. Using a similar nomenclature system, the Zipper embodiment can be referred to as a “1×1” embodiment, and the Keyhole A and Keyhole B embodiments can be referred to as “1×2” embodiments.

The number of Interlaced embodiments of the present disclosure is limited only by practical considerations. For example, “3×4”, “4×5” and “5×6” embodiments can all be manufactured as described above. Medical preferences from among the many options available may be developed over time in a procedure-specific manner.

The invention claimed is:

1. A two-component device for closing a wound or incision, comprising:

a) a first elongated component comprising:

i) a first flat flexible attaching member comprising a wound edge and a lower surface, the lower surface having an adhesive layer, the adhesive layer being protected by one or more release liners prior to application; and ii) one or more first lateral translation elements, each of the one or more first lateral translation elements comprising two or more first elongated connectors attached to a single first pulling element;

b) a second elongated component comprising:

i) a second flat flexible attaching member comprising a wound edge and a lower surface, the lower surface of the second flat flexible attaching member having an adhesive layer, the adhesive layer of the lower surface of the second flat flexible attaching member being protected by one or more release liners prior to application;

ii) a second lateral translation element comprising two or more second elongated connectors attached to a single second pulling element; and iii) a third lateral translation element comprising two or more third elongated connectors attached to a single third pulling element;

c) means for attaching the two or more first elongated connectors to the second flat flexible attaching member during closure, the attachment of the two or more first elongated connectors to the second flat flexible attaching member forms an attached portion and a bridging portion for each of the two or more first elongated connectors; and d) means for attaching the two or more second elongated connectors and the two or more third elongated connectors to the first flat flexible attaching member during closure, the attachment of the two or more second elongated connectors and the two or more third elongated connectors to the first flat flexible attaching member forms an attached portion and a bridging portion for each of the two or more second and the two or more third elongated connectors, wherein one of the two or more first elongated connectors, of the first elongated component, passes through a void formed between two of the two or more second elongated connectors, of the second elongated component, thereby causing the first and second elongated components to become linked and inseparable without cutting or breaking.

2. The two-component device of claim 1, wherein the first and second flat flexible attaching members are produced from an inelastic stock or from an elastic stock reinforced with an inelastic structural material.

3. The two-component device of claim 1, wherein the first and second flat flexible attaching members are produced from a vapor-permeable stock.

4. The two-component device of claim 1, wherein the single first pulling element is reinforced with a pull bar.

5. The two-component device of claim 1, wherein the means for attaching the two or more first and second elongated connectors to the second and first flat flexible attaching members during closure comprises an adhesive.

6. The two-component device of claim 5, wherein the adhesive is protected by the one or more release liners of the first flat flexible attaching member and/or the second flat flexible attaching member.

7. The two-component device of claim 6, wherein the one or more release liners of the first flat flexible attaching member and/or the second flat flexible attaching member are coded to indicate a sequence of removal.

8. The two-component device of claim 1, wherein the adhesive layer, on the lower surface of each of the first and second flat flexible attaching members, is protected by a first and second release liner of the one or more release liners of each of the first and second flat flexible attaching members, the first release liner protecting the adhesive layer along the lower surface adjacent the wound edge, and the second release liner protecting the adhesive layer along a remaining parallel section of the lower surface separated from the wound edge, the second release liner being separated from the wound edge by the first release liner.

9. The two-component device of claim 1, wherein the first and second flat flexible attaching members are provided with a wound edge bar.

10. The two-component device of claim 1, wherein the wound edges of the first and second flat flexible attaching members are curved or angled to evert skin edges.

11. The two-component device of claim 1, wherein the two or more first and the two or more second elongated connectors are sufficiently spaced-apart relative to each other to facilitate lateral adjustment of the first elongated component relative to the second elongated component.

12. The two-component device of claim 1, wherein the first and second flat flexible attaching members are produced from an elastic polymeric material not reinforced with an inelastic structural material.

* * * * *